United States Patent [19]

Shibuya et al.

[11] Patent Number: 5,578,469
[45] Date of Patent: Nov. 26, 1996

[54] PROCESS FOR PREPARING NEOTREHALOSE, AND ITS USES

[75] Inventors: Takashi Shibuya; Hiroto Chaen; Shuzo Sakai; Toshio Miyake, all of Okayama, Japan

[73] Assignee: Kabushiki Kaisha Hayashibara Seibutsu Kagaku Kenkyujo, Okayama, Japan

[21] Appl. No.: 22,340

[22] Filed: Feb. 24, 1993

[30] Foreign Application Priority Data

Feb. 25, 1992 [JP] Japan .................................. 4-093936

[51] Int. Cl.$^6$ .............................. C12P 1/04; C12P 19/12; A61K 38/43; A61K 38/46
[52] U.S. Cl. ........................ 435/100; 435/170; 435/839; 424/94.1; 424/94.6
[58] Field of Search ................................ 435/100, 170, 435/839; 424/94.1, 94.6

[56] References Cited

U.S. PATENT DOCUMENTS

| | | | |
|---|---|---|---|
| 4,487,198 | 12/1984 | Miyake et al. | 127/46.3 |
| 4,521,252 | 6/1985 | Miyake et al. | 127/46.3 |
| 5,218,096 | 6/1993 | Shibuya et al. | 435/74 |

FOREIGN PATENT DOCUMENTS

| | | |
|---|---|---|
| 0558213 | 9/1993 | European Pat. Off. . |
| 58-23799 | 2/1983 | Japan . |
| 58-72598 | 4/1983 | Japan . |
| 63-216492 | 9/1988 | Japan . |
| 4179490 | 6/1992 | Japan . |

OTHER PUBLICATIONS

*Enzyme Nomenclature*–1984, Academic Press, Inc., International Union of Biochemistry. pp. 306–309.
Walter N. Haworth et al, "Synthesis of a New Disaccharide, Neotrehalose", pp. 2847–2850: Journal of Chemical Society (1931).
Violet E. Sharp et al., "Synthesis of Trehalose–Type Disaccharides", pp. 285–288: Journal of Chemical Society (1951).

Kazuo Matsuda, "Studies on the Disaccharides in Koji Extract and Sake. Part IV. Isolation and Identification of α.α.–and α-β-Trehalose", pp. 119–123: Nippon Nogeikagaku Kaishi, vol. 30, (1959).

Zivko L. Nikolov et al., "Kinetics, Equilibria, and Modeling of the Formation of Oligosaccharides from D–Glucose with *Aspergillus niger* Glucoamylases I and II", pp. 694–704: Biotechnology and Bioengineering, vol. 34, (1989).

Denpun Handbook (Starch Handbook), pp. 106–108 (1967), edited by Jiro Nikuni, published by Asakura Publishing Co., Tokyo, Japan (1967). English translation of p. 108, lines 5–12.

*Primary Examiner*—John W. Rollins
*Assistant Examiner*—Kristin K. Larson
*Attorney, Agent, or Firm*—Browdy and Neimark

[57] ABSTRACT

Disclosed are a novel preparation of neotrehalose and its uses. The preparation comprises allowing α-amylase to act on an amylaceous substance to form neotrehalose, and recovering said neotrehalose. The neotrehalose has a satisfiable chemical stability, as well as other properties such as a sweetness, energy-imparting ability, osmosis-regulating ability, filler-imparting ability, gloss-imparting ability, moisture-retaining ability, viscosity-imparting ability, crystallization-preventing ability, and non-fermentability. These properties render the neotrehalose advantageously useful in preparations of a variety of compositions.

12 Claims, 2 Drawing Sheets

PROCESS FOR PREPARING NEOTREHALOSE, AND ITS USES

FIELD OF THE INVENTION

The present invention relates to a process for preparing neotrehalose, and uses for neotrehalose. More particularly, the present invention relates to a process for preparing neotrehalose comprising treating an amylaceous substance with α-amylase to form neotrehalose, and recovering neotrehalose. The neotrehalose so produced can be used in food compositions and pharmaceuticals.

DESCRIPTION OF THE PRIOR ART

Neotrehalose has long been known as a disaccharide of the formula O-α-D-glucopyranosyl β-D-glucopyranoside, or O-β-D-glucopyranosyl α-D-glucopyranoside. This saccharide possesses a rich sweetness, is readily water soluble, is non-reducing, and has satisfactory stability. Because of these characteristics, it is useful in products such as beverages, processed foods, tobaccos and cigarettes.

As described by W. H. Haworth in *Journal of the Chemical Society*, pp. 2847–2850 (1931) and by V. E. S. Sharp, ibid., pp. 285–288 (1951), synthetic chemical preparations of neotrehalose are known. However, there are still many problems to be overcome before neotrehalose can be produced safely and in sufficient yield to make the use of neotrehalose commercially viable.

Methods of preparing neotrehalose safely from natural sources or using biochemical synthesis of neotrehalose have been proposed. For example, Matsuda reported in *Nippon Nogeikakagaku Kaishi* Vol, 30, pp. 119–123 (1959) that a small amount of neotrehalose is present in a kojic extract together with isomaltose and kojibiose. According to this article, neotrehalose is prepared by subjecting a non-fermentable saccharide contained in a kojic extract to column chromatography using a carbon, recovering a disaccharide-rich fraction, treating this fraction with phenylhydrazine, separating the resulting sediment with a filter, acetylating saccharides in the filtrate to obtain a crystalline disaccharide octaacetate, and deacetylating the resulting crystal. Z. L. Nikolov et al. in *Biotechnology and Bioengineering*, Vol. 34, p. 694–704 (1989) revealed that neotrehalose is formed from glucose in a yield of 0.43 w/w % (hereinafter the symbol w/w % is abbreviated as "%", unless specified otherwise) when subjected to the condensing action of glucoamylase.

Kobayashi et al. disclose in Japanese Patent Laid-Open No. 216,492/88 a method for preparing neotrehalose along with centose which comprises treating an amylaceous substance with a cyclodextrin-forming enzyme. This publication notes that high performance liquid chromatography (HPLC) analysis revealed that a reaction mixture prepared by allowing a cyclodextrin-forming enzyme to act on an amylaceous substance contained 18.6% neotrehalose and 20.0% centose, dry solids basis (hereinafter d.s.b.); and that paper chromatography analysis revealed that the resultant neotrehalose-rich fraction contained about 20% nigerose, kojibiiose and iosmaltose, d.s.b. These authors also proposed to prepare neotrehalose from the reaction mixture by deactivating the remaining enzyme in the reaction mixture, simultaneously adding glucoamylase and yeast to the mixture in order to assimilate and remove the formed glucose, removing the yeast, adding sodium hydroxide to the mixture, autoclaving the resulting mixture, neutralizing the autoclaved mixture, and subjecting the neutralized mixture to column chromatography and/or sedimentation with an organic solvent.

The above two methods of preparation require complicated purification steps, and the yields of neotrehalose are so low that they have not yet been practiced on an industrial scale.

The present inventors disclosed in Japanese Patent application No. 307,054/90, a process for preparing neotrehalose, and uses for the neotrehalose, which comprises treating lactoneotrehalose (O-β-galactopyranosyl-(1->4)-O-β-D-glucopyranosyl α-D-glucopyranoside) in order to form neotrehalose, and recovering the neotrehalose. This process provides a method for preparing neotrehalose in a relatively high yield as compared with the starting material, lactoneotrehalose, although some problems remained in the preparation of neotrehalose.

There has been a great demand for a safe method for preparing neotrehalose which produces neotrehalose in a high yield.

SUMMARY OF THE INVENTION

The present inventors have studied enzymes which hydrolyze amylaceous substances in order to obtain an improved method for preparing neotrehalose. As a result of this study, the present inventors found that neotrehalose can be produced by treating an amylaceous substance with α-amylase (EC 3.2.1.1.) to form neotrehalose. Thus, the present invention was accomplished.

DETAILED DESCRIPTION OF THE INVENTION

The present invention relates to a process for preparing neotrehalose, and to uses for neotrehalose. More particularly, the present invention relates to a process for preparing neotrehalose by treating an amylaceous substance with α-amylase to form neotrehalose, and recovering the neotrehalose so formed. The present invention also relates to compositions such as food products and pharmaceuticals which contain said neotrehalose.

The amylaceous substances which can be used in the present invention are starch and its partial hydrolysates, or, usually, those amylaceous substances having a dextrose equivalent (DE) of about 70 or less. Examples of such amylaceous substances are gelatinized starch, liquefied starch, solubilized starch, partial starch hydrolyzates, and amylaceous saccharide-transferred products. Amylaceous substances from roots such as potato, tapioca and sweet potato and amylaceous substances derived from aboveground plants such as corn, wheat and rice are also suitable for use in the invention as a source of starch.

The starch hydrolyzates which can be used in the present invention are high molecular weight products such as amylose and dextrins, as well as one or more maltooligosaccharides such as maltose, maltotriose, maltotetraose, maltopentaose, maltohexaose, maltoheptaose and maltooctaose.

The α-amylases which can be used in the present invention are those which can form neotrehalose when they act on amylaceous substances. For example, α-amylases derived from microorganisms of the genera Bacillus and Aspergillus can be used. Among these α-amylases, a saccharogenic α-amylase obtained from the microorganisms of the species *Bacillus subtilis* is particularly useful because this α-amylase formed neotrehalose in a relatively high yield, making it advantageous for use in industrial scale production of neotrehalose.

As described in *Denpun Handbook* (*Starch Handbook*), pp. 106–108, edited by Jiro Nikuni, (1967), the above-mentioned saccharogenic α-amylase is an α-amylase which has an extremely high power of saccharification as compared with its power of dextrinogenisis.

Any enzymatic reaction can be used in the present invention as long as it forms neotrehalose. For example, when using a saccharogenic α-amylase derived from microorganisms of the species *Bacillus subtilis*, neotrehalose is formed by subjecting an aqueous solution containing an amylaceous substance such as partial starch hydrolyzates to the action of from 1–1000 units/g amylaceous substance, based upon the weight of the dry solid basis (d.s.b.) of the saccharogenic α-amylase. In this case, the enzymatic reaction is effected under the conditions selected from a concentration in the range of 1–80%, d.s.b., preferably 20–70%, d.s.b., of amylaceous substances; a temperature in the range of 20°–80° C.; a pH in the range of 3–9; and a reaction time in the range of 1–100 hours. If necessary, immobilized α-amylase can be used repeatedly. Reaction mixtures so obtained can be treated with glucoamylase of β-amylase to form and accumulate neotrehalose and α-glycosyl neotrehalose.

The resulting solutions containing neotrehalose, formed by the above-noted enzymatic reaction, usually contain about 5–15% neotrehalose, d.s.b. These solutions can be used in the form of a liquid, a syrup, or a solid after filtration, purification, and optional concentration and drying. In order to improve the inherent properties of neotrehalose, the solutions are generally separated and purified so as to have a high content of neotrehalose prior to use. Examples of filtration and purification methods which can advantageously be used in the present invention are fermentation using yeasts, membrane filtration, separation and sedimentation, crystallization and column chromatography, in which concomitant saccharides are separated and removed.

More particularly, as disclosed in Japanese Patent Laid-Open Nos. 23,799/83 and 72,598/88, column chromatography in which a strongly acidic cation exchange resin is used can be used to remove concomitant saccharides in a neotrehalose solution and to obtain a neotrehalose-rich fraction. In this case, a fixed-bed method, a moving-bed method, or a semi-moving bed method can be appropriately used. The solution having a high concentration of neotrehalose thus obtained can be concentrated to form a more concentrated solution of neotrehalose which can be used to prepare crystalline neotrehalose by the method disclosed in Japanese Patent Application No. 307,054/90.

The neotrehalose produced according to the present invention is a disaccharide which is non-reducing, possessing a satisfactory stability for use in foods and pharmaceuticals, as well as a rich sweetness. These properties render the neotrehalose easy to handle in preparing compositions therefrom. As disclosed in Japanese Patent Application No. 268,683/91, applied for by the present inventors, neotrehalose is orally or parenterally administered to a recipient and is well metabolized and advantageously utilized by the recipient as an energy supplement without fear of toxicity or causing undesirable side effects. Since neotrehalose is not readily fermented by microorganisms which induce dental caries, it can be used as a sweetener which causes substantially no dental caries. Furthermore, neotrehalose is a stable sweetener, which stability renders it useful as a sugar-coating agent for tablets when the neotrehalose is combined with a binder such as pullulan and hydroxyethyl starch. In addition, neotrehalose is chemically stable, and can be used with other saccharides to regulate their osmotic pressure and to improve their characteristics with respect to filling, imparting gloss, retaining moisture, imparting viscosity, reducing their fermentability, and preventing their crystallization.

Because of the advantageous properties of neotrehalose, neotrehalose can be used as a sweetener, a taste-improving agent, a quality-improving agent and a stabilizer in compositions such as food products, tobaccos, cigarettes, feeds, pet foods, cosmetics and pharmaceuticals.

Compositions prepared according to the present invention are those which contain a sufficient amount of neotrehalose to exhibit the desired properties of neotrehalose in the compositions. In general, 5% or more, preferably 10% or more or neotrehalose, d.s.b, can be incorporated into a product to exert a satisfactory effect.

Compositions according to the present invention can be those prepared with only neotrehalose, and those prepared with neotrehalose in combination with one or more other substances. These other substances include nutritional substances such as proteins, amino acids, lipids, vitamins and minerals; as well as substances such as antiseptics, enzymes, hormones, and cytokines, which can be formulated with neotrehalose. If necessary, in preparing these compositions, one or more additional substances can be included, such as flavoring agents, coloring agents, stabilizers, fillers, and vehicles, prior to completion of the processing. The resulting compositions can be advantageously prepared to conform to their ultimate use. The compositions so obtained can be administered orally or parenterally.

The methods used to incorporate neotrehalose in a product according to the present invention are those which incorporate neotrehalose in the product before completion of processing the product. For example, conventional methods such as mixing, kneading, dissolving, melting, soaking, spreading, applying, coating, spraying, injecting, crystallizing, and solidifying, can be used.

The following Experiments explain the preparation of neotrehalose according to the present invention using α-amylase.

EXPERIMENT 1

Screening of Neotrehalose-forming Enzyme

A saccharogenic α-amylase, an α-amylase (EC 3.2.1.1) specimen commercialized by Ueda Chemical Co. Ltd., Osaka, Japan; a β-amylase (EC 3.2.1.2) specimen commercialized by Nagase Biochemicals, Ltd., Kyoto, Japan; "GLUCOZYME", a glucoamylase (EC 3.2.1.3) specimen commercialized by Nagase Biochemicals, Ltd., Kyoto, Japan; an α-glucosidase (EC 3.2.1.20) specimen derived from rice commercialized by Seikagaku-Kogyo Co., Ltd., Tokyo, Japan; and an isoamylase (EC 3.2.1.68) specimen commercialized by Hayashibara Biochemical Laboratories Inc., Okayama, Japan, were used in this experiment.

One thousand units per gram of maltose, d.s.b., of each enzyme was added to a 33% aqueous solution (pH 6.0) containing "MALTOSE HHH", a maltose product commercialized by Hayashibara Biochemical Laboratories Inc., Okayama, Japan. The solution containing the maltose was subjected to the action of the enzyme at 55° C. for 24 hours. The enzymatic reaction was stopped by heating the solution at 100° C. for ten minutes. Each reaction mixture was diluted with 20 mM acetate buffer (pH 4.5) to form a solution having a concentration of about 5% d.s.b., to which was added 20 units per gram of maltose, d.s.b., of glucoamylase, and the solution was then subjected to an enzymatic reaction at 40° C. for 24 hours. The presence of neotrehalose in each reaction mixture was determined by HPLC using "PA-03", a column produced by YMC Co., Ltd., Kyoto, Japan, using a 70 v/v % aqueous solution of acetonitrile as an eluate. The results were as shown in Table 1.

TABLE 1

| Enzyme | Neotrehalose content |
| --- | --- |
| α-Amylase (EC 3.2.1.1) | ++ |
| β-Amylase (EC 3.2.1.2) | − |
| Glucoamylase (EC 3.2.1.3) | + |
| α-Glucosidase (EC 3.2.1.20) | + |
| Isoamylase (EC 3.2.1.68) | − |

The symbol "−" means that neotrehalose was not formed.
The symbol "+" means that the amount of neotrehalose formed was less than 5% as compared with the starting materials, on a dry solids basis.
The symbol "++" means that the amount of neotrehalose formed was 5% or more as compared with the starting materials, on a dry solids basis.

As shown in Table 1, glucoamylase, αglucosidase, and α-amylase formed neotrehalose. As noted in a previous publication, glucoamylase and αglucosidase formed a very small amount of neotrehalose. Alpha-amylase formed a large amount of neotrehalose. This is a new finding, and it is a novel discovery.

Based upon the fact that α-amylase produces large quantities of neotrehalose, as compared to other enzymes, the present inventors studied α-amylases which form satisfactory amounts of neotrehalose.

EXPERIMENT 2

Screening of Neotrehalose-forming α-amylase

A saccharogenic α-amylase specimen commercialized by Ueda Chemical Co., Ltd., Osaka, Japan; maltotetraose-forming amylase commercialized by Hayashibara Co., Ltd., Okayama, Japan; "SUMIZYME L", a Taka amylase specimen commercialized by Shin Nihon Chemical Ind., Tokyo, Japan; and "NEO-SPITASE" and "SPITASE HS", both of which are themostable liquefying α-amylase specimens commercialized by Nagase Biochemicals Ltd., Kyoto, Japan, were used in this experiment as an α-amylase. In a manner similar to that of Experiment 1, the presence of neotrehalose was examined, and the results were as shown in Table 2.

TABLE 2

| α-Amylase | Neotrehalose content |
| --- | --- |
| Saccharogenic α-Amylase | ++ |
| Maltotetraose-forming enzyme | ± |
| Taka amylase | + |
| Thermostable liquefying α-amylase (NEO-SPITASE) | ± |
| Thermostable liquefying α-amylase (SPITASE HS) | ± |

The symbol "−" means that neotrehalose was not formed.
The symbol "±" means that the amount of neotrehalose formed was a trace amount.
The symbol "+" means that the amount of neotrehalose formed was less than 5% as compared with the starting materials, on a dry solids basis.
The symbol "++" means that the amount of neotrehalose formed was 5% or more as compared with the starting materials, on a dry solids basis.

As shown in Table 2, all of the α-amylases used formed neotrehalose in a variety of amounts. Among these α-amylases, the saccharogenic α-amylase formed a relatively large amount of neotrehalose.

EXPERIMENT 3

Preparation of Neotrehalose Using α-amylase

Figure 1:
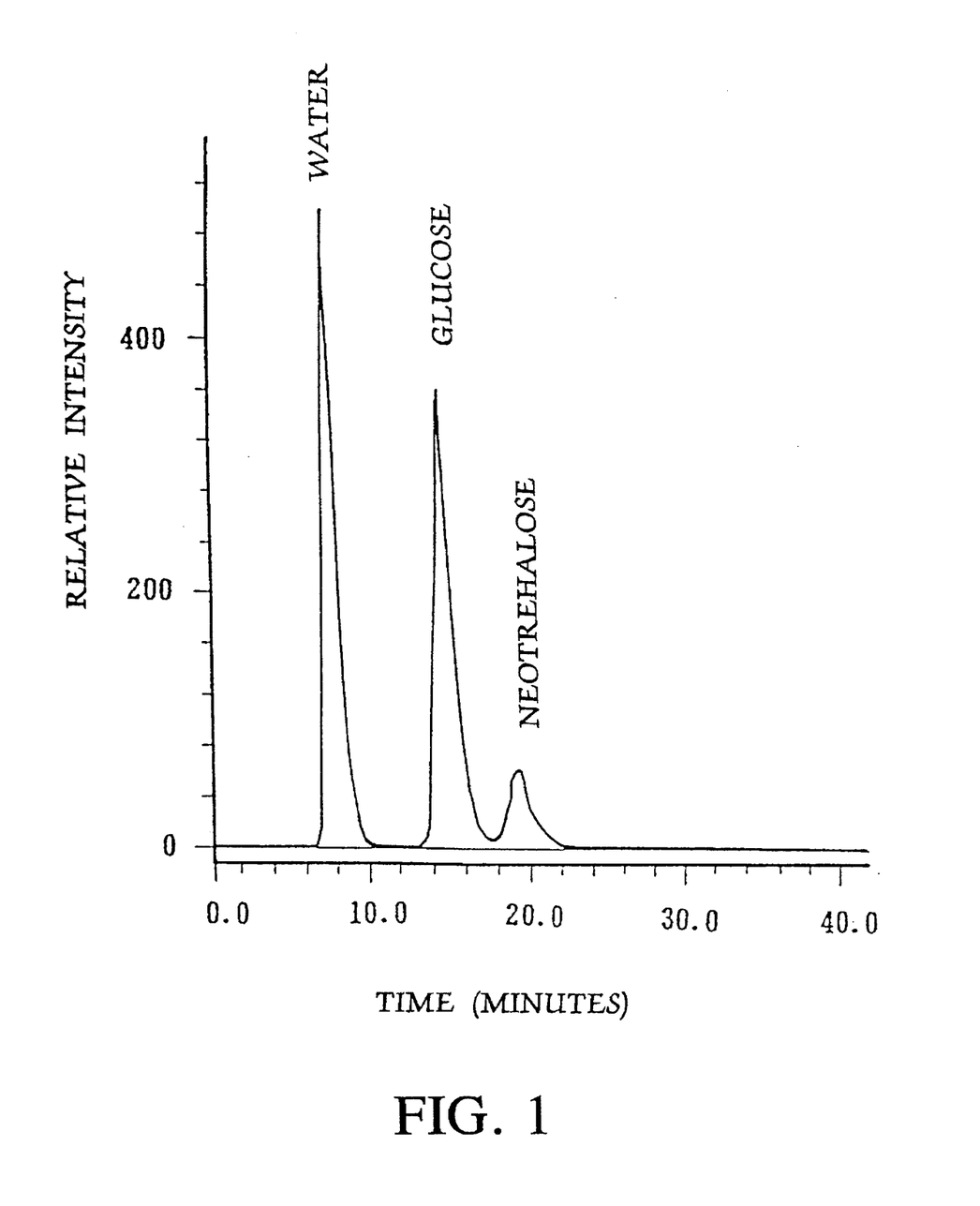
FIG. 1 shows a chromatogram of an enzymatic reaction mixture on HPLC.

Fifty parts by weight of "MALTOSE H", a maltose commercialized by Hayashibara Biochemical Laboratories Inc., Okayama, Japan, was dissolved by heating in 50 parts by weight of water, and the solution was heated to 60° C., adjusted to pH 5.2, and 100 units/gram of maltose, d.s.b., of a saccharogenic α-amylase specimen derived from *Bacillus subtilis*, a crystalline enzyme commercialized by Seikagaku-Kogyo Co., Let., Tokyo, Japan, was added and the mixture was allowed to react for 20 hours. This mixture was heated at 100° C. for ten minutes to deactivate the remaining enzyme. The resulting mixture was heated to 55° C., adjusted to pH 4.5, and 20 units of "GLUCOZYME" per gram of solid matter was added. This mixture was allowed to react enzymatically for 16 hours. Thereafter, the reaction mixture was heated at 100° C. for 15 minutes to deactivate the remaining enzyme. As in Experiment 1, the resulting solution was subjected to HPLC, and the chromatogram was as shown in FIG. 1 in which the ordinate indicates refractive intensity (RI) and the abcissa indicates time. The solution contained about 12% neotrehalose on a dry solids basis.

The solution was decolorized with activated charcoal, and was then desalted and purified with an ion-exchange resin ($H^+$ and $OH^-$ form). This purified solution was concentrated to a concentration of about 40%, dry solids basis, and subjected to column chromatography in which an ion exchange resin was used to recover a fraction rich in neotrehalose. "AMBERLITE XT-1016 ($Na^+$ form)" ion exchange resin, a strongly acidic cation exchange resin commercialized by Japan Organo Co., Ltd., Tokyo, Japan, was used as a resin for fractionation. In this fractionation, the resin was suspended in water and packed in a jacketed stainless steel column having an inner diameter of 5.4 cm. Four columns having a gel-bed depth of 5 m wee cascaded in series to give a total gel-bed depth of about 20 m. The inner column temperature was kept at 55° C., and 5 v/v % of a material saccharide solution having a concentration of about 40%, d.s.b was added The columns were fed with 55° C. water at a flow rate of space velocity (SV) of 0.3 to effect fractionation, followed by recovery of a neotrehalose rich fraction. A portion of the fraction containing about 85% neotrehalose, d.s.b, was concentrated into a solution having a concentration of about 75%, d.s.b., which was then allowed to stand at 20° C. overnight to form a crystal. The resultant crystal was added as a seed crystal to a solution of above 72% neotrehalose, d.s.b., which had been prepared from the neotrehalose-rich fraction, and the resulting mixture was gently stirred to effect crystallization. The resulting massecuite was separated to obtain a crystal which was then washed by spraying it with a small amount of water to obtain a high purity crystal. The resulting crystal was dissolved in water, and recrystallized as above. The crystals were separated to produce crystalline neotrehalose with a purity of 99.9%, d.s.b.

EXPERIMENT 4

Physicochemical Properties of Neotrehalose

The physicochemical properties of neotrehalose were determined using a high purity crystalline neotrehalose prepared by the method described in Experiment 3. As a result, the physicochemical properties were the same as those shown in Japanese Patent Application No. 307,054/90, which was applied for by the present inventors.

The following Examples A and B will explain the present preparation of neotrehalose and compositions containing said neotrehalose.

EXAMPLE A-1

Five parts by weight of "PINE-DEX #4", a dextrin product (having a dextrose equivalent of 18) commercialized by Matsutani Chemical Ind. Co., Ltd., Kyoto, Japan, was dissolved by heating in five parts by weight of water. The solution was adjusted to pH 5.6, heated to 60° C., and 100 units/gram of dextrin, d.s.b, of a saccharogenic α-amylase specimen commercialized by Ueda Chemical Co., Ltd., Osaka, Japan, was added. This mixture was allowed to react enzymatically for 20 hours. Thereafter, the resulting mixture was heated to deactivate the remaining enzyme. The reaction mixture was decolorized in a conventional manner with activated charcoal, and desalted and purified with an ion exchange resin ($H^+$ and $OH^-$ form). The resulting solution was concentrated to obtain a syrup having a concentration of about 75% d.s.b., with a yield of about 93% of theoretical. The product contains about 10% neotrehalose, d.s.b., and possesses a rich sweetness, appropriate viscosity and moisture-retaining ability. Because of these properties, the product can be used advantageously in a variety of compositions.

EXAMPLE A-2

Example A-2(1)

Preparation of Enzyme

A seed culture of a microorganism of the species *Bacillus subtilis* IFO 14140 (Fukumoto D11) was inoculated to a liquid culture medium as shown below, and incubated at 27° C. for three days. The broth was separated by centrifugation, and the resultant supernatant was added along with ammonium sulfate. The mixture was allowed to stand overnight in a cooling room, and subjected to centrifugation, followed by recovery of the sediment. The resulting sediment was added along with a small amount of 0.1M phosphate buffer (pH 7.0) to dissolved the formed enzyme. The resulting solution was used as an enzyme specimen with an enzyme activity of 340 U/ml.

| Liquid culture medium (pH 7.0) | |
| --- | --- |
| Solubilized starch | 3.0% |
| Diammonium hydrogenphosphate | 1.0% |
| Corn steep liquor (CSL) | 1.0% |
| Yeast extract | 0.1% |
| Polypeptone | 0.1% |

Throughout the specification, the enzyme activity, i.e., a power of saccharification, is determined by adding 0.2 ml of an enzyme solution to 5 ml solution of 1% solubilized starch in 20 mM acetate buffer (pH 5.5), subjecting the resulting mixture to enzymatic reaction at 40° C. for ten minutes, and measuring the amount of reducing sugars formed by the Somogyi-Nelson method. One unit of enzyme activity is defined as the amount of enzyme which releases one μmol glucose per minute at 40° C.

EXAMPLE A-2

Example A-2(2)

Enzymatic Reaction

Figure 2:
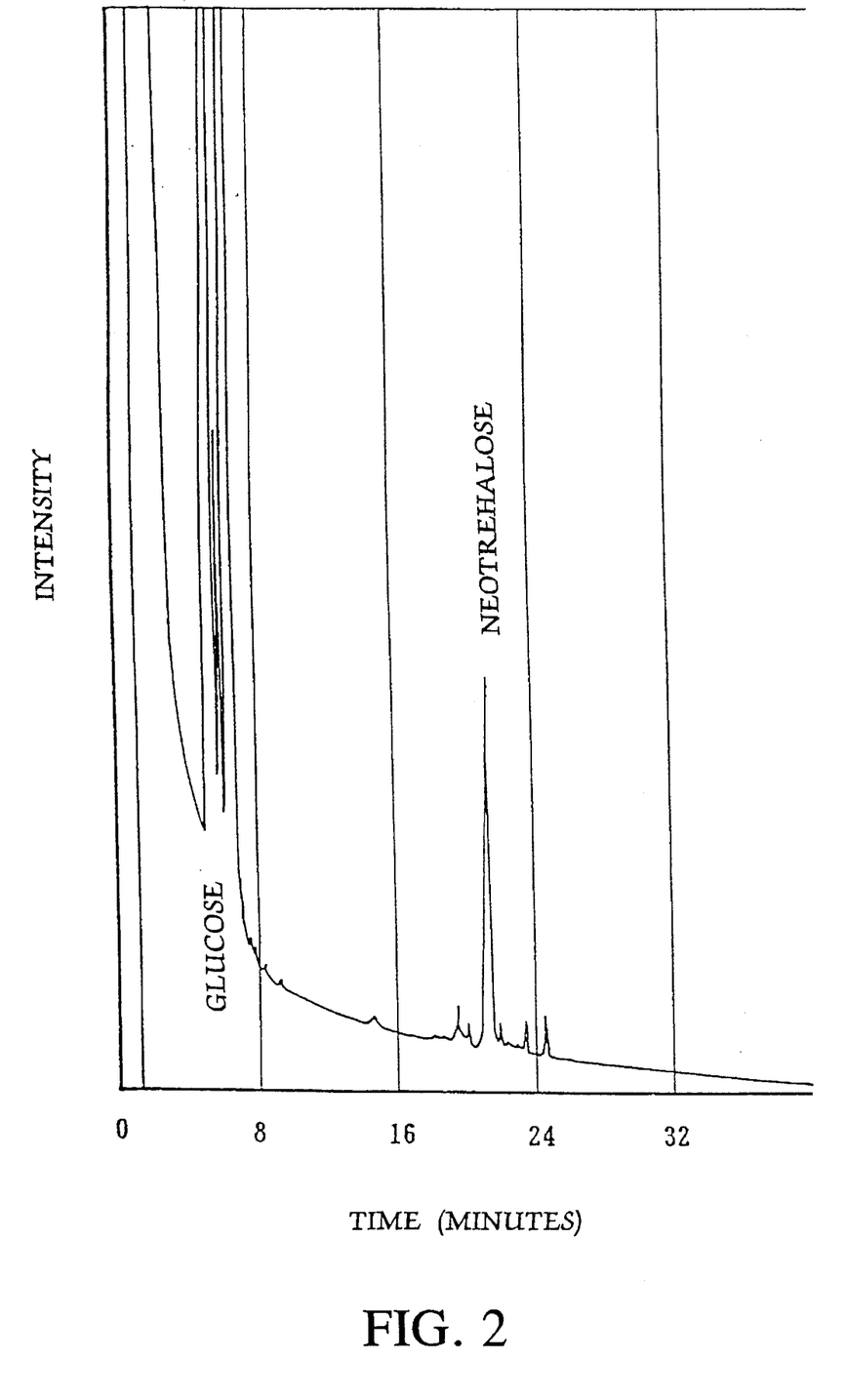
FIG. 2 shows a chromatogram of an enzymatic reaction mixture on gas chromatography.

Fifty parts by weight of "MALTOSE H", a maltose product commercialized by Hayashibara Biochemical Laboratories Inc., Okayama, Japan, was added to 50 parts by weight of water. The maltose was dissolved in the water by heating. To the resulting solution was added 50 units per gram of maltose, d.s.b, of the enzyme specimen prepared in Example A-s-(1). The mixture was subjected to an enzymatic reaction at pH 5.5 and 55° C. for 24 hours. The vessel containing the mixture was placed into boiling water for ten minutes to stop the enzymatic reaction. The mixture thus obtained was diluted with water to give a concentration of about 1%, d.s.b. Then, 20 units/g maltose, d.s.b., of glucoamylase was added and the mixture was subjected to enzymatic reaction at pH 4.5 at 40° C. for 24 hours. The reaction mixture thus obtained was subjected to gas chromatographic analysis. The results were as shown in FIG. 2. IN FIG. 2, the ordinate is the intensity determined with a flame ionization detector, and the abcissa shows time.

The reaction mixture contained 7.2% neotrehalose, d.s.b. The reaction mixture was decolorized in a conventional manner, desalted, and purified with an ion exchange resin ($H^+$ and $OH^-$), and concentrated to about 40% solution, d.s.b, which was then subjected to column chromatography as in Experiment 1 to produce a neotrehalose-rich fraction containing 52% neotrehalose, d.s.b. The product has a rich sweetness and an appropriate viscosity and moisture-retaining ability. Because of these properties, the product can be used in a variety of compositions.

EXAMPLE A-3

Sixty parts by weight of "SUNMALT®", a maltose product commercialized by Hayashibara Co., Ltd., was dissolved by heating in 40 parts by weight of water, and the solution was heated to 60° C., adjusted to pH 5.2, and 200 units/gram maltose, d.s.b., of a saccharogenic α-amylase specimen commercialized by Ueda Chemical Co., Ltd., Osaka, Japan, was added. The mixture was subjected to an enzymatic reaction for 36 hours. Thereafter, the reaction mixture was heated to deactivate the remaining enzyme. The resulting mixture was diluted to give a concentration of about 20%, d.s.b., adjusted to pH 5.0, and 10 units/gram of maltose, d.s.b., of glucoamylase were added. The mixture was subjected to an enzymatic reaction for 40 hours. Thereafter, the reaction mixture was heated to deactivate the remaining enzyme.

The mixture thus obtained was decolorized with activated charcoal in a conventional manner, desalted and purified with an ion exchange resin ($H^+$ and $OH^-$ form), and concentrated into a solution having a concentration of about 60%, d.s.b. The solution was subjected to column chromatography in a manner similar to that of Experiment 1, except that in this case "CG 6000 ($Na^+$-form)" ion exchange resin, a strongly acidic cation exchange resin commercialized by Japan Organo Co., Ltd., Tokyo, Japan, as used as a resin for fractionation. The resulting solution was subjected to column chromatography to obtain a neotrehalose-rich fraction containing about 90% neotrehalose d.s.b. The fraction was concentrated to give a concentration of about 76%, d.s.b., placed in a crystallizer, and about 2% seed crystal, d.s.b, was added to obtain a massecuite having about 45% crystal, d.s.b. The massecuite was sprayed from a nozzle located on the upper part of a drying tower at a pressure of 150 kg/cm², and collected on a metal wire conveyor provided in the lower part of the spraying tower while sending hot air at 85° C. from the upper part of the spraying tower to the lower part of the spraying tower. The resulting crystalline powder collected on the conveyer was gradually removed from the drying tower while sending heated air at 45° C. from under the conveyor. The crystalline powder was injected into an ageing tower and aged for ten hours while heated air was sent thereto to complete the crystallization and drying. Thus, a crystalline neotrehalose powder containing other saccharides was obtained. The product is easy to handle without exhibiting substantial hygroscopicity, and these properties render the product useful in a variety of compositions as a sweetener, stabilizer, taste improving agent, and quality improving agent.

EXAMPLE A-4

A solution containing about 10% neotrehalose, d.s.b, prepared by the method of Example A-1 was diluted to give a concentration of about 10%, d.s.b., adjusted to pH 4.6, and 30 units per gram of dextrin, d.s.b, of glucoamylase were added. The mixture was subjected to an enzymatic reaction for 16 hours. The reaction mixture was heated to deactivate the remaining enzyme. The resulting solution was decolorized in a conventional manner with activated charcoal, desalted and purified with an ion exchange resin ($H^+$ and $OH^-$ form), and concentrated to a concentration of about 45%, d.s.b. The resulting solution was subjected to column chromatography to produce a fraction rich in neotrehalose using the method of Experiment 1, except that "DOWEX 50W-X4", a strongly acidic cation exchange resin commercialized by Dow Chemical Co., Midland, Mich., U.S.A., was used as a resin for fractionation. The fraction containing about 85% neotrehalose, d.s.b, was concentrated to give a concentration of about 85%, d.s.b, fed to a crystallizer, allowed to stand at 20° C. for four days to effect crystallization and solidification. The solid product so obtained was pulverized with a pulverizer and dried to produce a neotrehalose powder containing other saccharides. The product is easy to handle without exhibiting substantial hygroscopicity, and these render it useful in a variety of compositions as a sweetener, stabilizer, taste-improving agent, and quality improving agent.

EXAMPLE B-1

Sweetener

One part by weight of a crystalline neotrehalose powder prepared by the method of Example A-3 was mixed to homogeneity with 0.05 parts by weight of "αG SWEET", an α-glycoysl stevioside product commercialized by Toyo Sugar Refining Co., Ltd., Tokyo, Japan, and the resultant mixture was fed to a granulator to obtain a sweetener in the form of granules. This product has twice the sweetening power of sucres, and the calories per sweetening power are half that of sucrose. The product is used to impart sweetness to low calorie food products for persons such as those who are overweight and/or diabetic or who are otherwise restricted in their sugar or calorie intake. Dental caries-inducing microorganism form less acid and insoluble glucans when they assimilate this product, and this renders the product useful as a sweetener for food products which prevent dental caries.

EXAMPLE B-2

Hard Candy

One hundred parts by weight of a sucrose solution having a concentration of 55% sucrose, d.s.b., was mixed while heating with 30 parts by weight of a syrup containing neotrehalose prepared by the method of Example A-2. The mixture was concentrated by heating to give a moisture content of less than 2%, and mixed with one part by weight of citric acid and adequate amounts of lemon flavor and coloring agent. The resulting mixture was formed into hard candy in a conventional manner. The candy, in which sugar crystallization is prevented, is a high quality hard candy having a satisfactory biting property and a good taste.

EXAMPLE B-3

Strawberry Jam

One hundred and fifty parts by weight of fresh strawberries, 60 parts by weight sucrose, 20 parts by weight maltose, 40 parts by weight of a syrup containing neotrehalose prepared by the method of Example A-2, five parts by weight of pectin, and one part by weight of citric acid were sufficiently boiled down in a vessel, and bottled to obtain strawberry jam. The jam is a satisfactory strawberry jam having a satisfactory flavor and color.

EXAMPLE B-4

Lactic Acid Beverage

Ten parts by weight of defatted milk was sterilized by heating at 80° C. for 20 minutes, and cooled to 40° C. Then, 0.3 parts by weight of a starter were added, and the mixture was allowed to ferment at about 37° C. for 10 hours. Thereafter, the resultant mixture was homogenized, four parts by weight of a crystalline neotrehalose powder prepared by the method of Example A-4 were added along with one part by weight of sucrose, and two parts by weight of an isomerized sugar syrup, and the mixture thus obtained was sterilized at 70° C., and cooled. An adequate amount of a flavoring agent was added, and the beverage was bottled to obtain a lactic acid beverage. The beverage is a high-quality lactic acid beverage having a well harmonized acidity with flavor and sweetness.

EXAMPLE B-5

Condensed Milk with Sugar

In 100 parts by weight of milk were dissolved three parts by weight of a syrup containing neotrehalose, prepared by the method of A-z, and one part by weight of sucrose. The resultant solution was sterilized by heating with a plate heater, concentrated to give a concentration of about 70%, d.s.b, and aseptically bottled to obtain the sweetened condensed milk. The sweetened condensed milk has a mild sweetness and a satisfactory flavor, which render it useful as a seasoning in foods for infants, fruits, coffee, cocoa and tea.

EXAMPLE B-6

Fruit Juice Powder

To thirty three parts by weight of a fruit juice powder, prepared by spray drying a fruit juice, was added 50 parts by weight of a crystalline neotrehalose powder prepared by the method of Example A-3, ten parts by weight of sucrose, 0.65 parts by weight of anhydrous citric acid, 0.1 part by weight of malic acid, 0.2 part by weight of L-ascorbic acid, 0.1 part by weight of sodium citrate, 0.5 parts by weight of pullulan, and an adequate amount of a powdered flavor. The resultant mixture was mixed to homogeneity, pulverized to obtain a pulverulent product which was then fed to a fluidized bed granulator, sprayed with a concentrated neotrehalose solution prepared by the method of Example A-3 as a binder, and granulated for 30 minutes while heated air at 40° C. was administered thereto at a flow rate of 150 m³/min. Thereafter, the resulting powder was weighed and packed to obtain a fruit juice powder. The fruit juice powder so produced contains about 30% fruit juice, d.s.b. The product is free of unsatisfactory odors, and the odor is stable for a relatively long period of time without absorbing moisture or solidifying.

EXAMPLE B-7

Chocolate

Forty parts by weight of cacao paste, 10 parts by weight of cacao butter, and 50 parts by weight of a crystalline neotrehalose powder prepared by the method of Example A-4 were passed through a refiner to lower the particle size fed to a conch, and kneaded at 50° C. over two days. During this kneading process, 0.5 parts by weight of lecithin was added to the mixture and dispersed throughout by mixing therein. Thereafter, the mixture was heated to 31° C. with a thermoregulator, poured into a molder immediately before the cacao butter solidified, deaerated with a vibrator, and passed through a tunnel kept at 10° C. for 20 minutes to effect solidification. The solidified product was removed from the molder and packed to obtain the chocolate. The chocolate has a satisfactory color, gloss and texture, a mild sweetness, and melts in the mouth without exhibiting substantially hygroscopicity.

EXAMPLE B-8

Chewing Gum

Three parts by weight of a gum base was melted by heating until it was softened, and admixed with four parts by weight of sucrose, three parts by weight of a crystalline neotrehalose powder prepared by the method of Example A-3, and adequate amounts of a flavoring agent and coloring agent. The resultant mixture was kneaded in a conventional manner with a roll, and formed and packed to obtain chewing gum. The gum has a satisfactory texture and flavor.

EXAMPLE B-9

Cream Filling

One hundred parts by weight of corn starch, 100 parts by weight of a syrup containing neotrehalose prepared by the method of Example A-2, 80 parts by weight of maltose, 20 parts by weight of sucrose, and one part by weight of salt were mixed to homogeneity, and the mixture was admixed with 280 parts by weight of egg. The resulting mixture was gradually added to 1000 parts by weight of boiling milk and stirred while heating. The heating was stopped when the corn starch had gelatinized to a semitransparent state, cooled, and vanilla flavor was added. The filling was weighed, injected, and packaged to produce a cream filling. The cream filling had a smooth gloss, mild sweetness and satisfactory taste.

EXAMPLE B-10

"Uiro-no-moto" (Premix of Sweet Rice Jelly)

Ninety parts by weight of rice powder, 20 parts by weight of corn starch, 120 parts by weight of a crystalline neotrehalose powder prepared by the method of Example A-4, and four parts by weight of pullulan were mixed to homogeneity to produce a premix of sweet rice jelly. The premix was kneaded with adequate amounts of water and powdered green tea, and the resulting mixture was placed into a vessel and steamed for 60 minutes to produce a sweet rice jelly with the powdered green tea. The jelly had a satisfactory gloss, biting property, and satisfactory taste. Starch retrogradation was inhibited in this product, so that the product has a relatively long shelf life.

EXAMPLE B-11

Solid Preparation for Intubation Feeding

A composition consisting of 500 parts by weight of a crystalline neotrehalose prepared by the method of Experiment 3, 270 parts by weight of powdered egg, 209 parts by weight o defatted milk powder, 4.4 parts by weight of sodium chloride, 1.8 parts by weight of potassium chloride, 4 parts by weight to magnesium chloride, 0.01 part by weight of thiamine, 0.1 part by weight of ascorbic acid, 0.6 parts by weight of vitamin E acetate, and 0.04 parts by weight of nicotinamide was prepared, and 25 g aliquots of the composition were injected into small moistureproof laminated bags. The bags were heat sealed to provide individual servings of a solid preparation to be diluted for intubation feeding.

To use this product for intubation feeding, one bag of the solid preparation is dissolved in about 150–200 ml water and administered to a patient orally or through the nasal cavity, stomach and/or intestines by intubation feeding. This preparation is useful as an energy supplement.

EXAMPLE B-12

Transfusion

Crystalline neotrehalose prepared by the method of Experiment 3 was dissolved in water at a concentration of 10 w/v %, and the resultant solution was membrane filtered in a conventional manner, aseptically injected into plastic bottles, and cap sealed to form a transfusion composition. The product is a stable transfusion composition which can be administered either intravenously or intraperitoneally to a recipient. A 10 w/v % solution of this transfusion composition is isotonic to blood so that this product can be used to supplement energy for a recipient at a 2-fold higher concentration than glucose.

EXAMPLE B-13

Transfusion

Crystalline neotrehalose prepared by the method of Experiment 3 and a composition of amino acids as tabulated below are respectively dissolved by mixing in water to form 5 w/v % and 3 w/v % solutions. Thereafter, the solutions were purified as in Example B-12, injected into plastic bags, and sealed to obtain a transfusion composition.

| Composition of amino acids | mg/100 ml |
|---|---|
| L-Isoleucine | 180 |
| L-Leucine | 410 |
| L-Lysine hydrochloride | 620 |
| L-Methionine | 240 |
| L-Phenylalanine | 290 |
| L-Threonine | 180 |

The above transfusion composition, which is a combination of a saccharide and amino acids, is stable and can be administered either intravenously or interaperitoneally to a recipient because the saccharide is neotrehalose, which is a non-reducing saccharide. The transfusion composition can be used as an energy supplement which also supplies amino acids.

EXAMPLE B-14

Ointment for Traumatic Injury

Five hundred parts by weight of a crystalline powder prepared by the method of Example A-4 was admixed with 50 parts by weight of methanol into which three parts by weight of iodine had been dissolved. This mixture was admixed with 200 parts by weight of a 10% aqueous solution of pullulan to obtain an ointment for traumatic injury which is spreadable and adhesive. The ointment reduces the healing time and completely heals the affected area because the iodine exerts a bactericidal action and the neotrehalose supplies energy to living cells.

EXAMPLE B-15

Sugar Coated Tablet

A 150 mg crude table used as the center of a tablet was sugar coated with a first solution consisting of 40 parts by weight of a crystalline neotrehalose prepared by the method of Experiment 3, 2 parts by weight of pullulan having an average molecular weight of 200,000 daltons, 30 parts by weight of water, 25 parts by weight of talc, and 3 parts by weight of titanium oxide until the coated tablet reached a mass of about 230 mg. The coated tablet was then coated with a second solution consisting of 65 parts by weight of the same neotrehalose as above, one part by weight of the same pullulan as above, and 34 parts by weight of water. This table was then further coated with a wax to obtain a sugar-coated tablet having a satisfactory gloss and appearance. The sugar coating steps are easily conducted, and the tablet has satisfactory tolerance to shock and retains its quality for a relatively long period of time. The tablet can be used as an energy supplement.

As is evident from the above, the present neotrehalose is prepared in relatively high yield by allowing α-amylase to act on an amylaceous substance to form neotrehalose, and the resulting neotrehalose can be readily separated and purified from the reaction mixture. The neotrehalose thus obtained is a non-reducing disaccharide which has an excellent stability and a rich, high quality sweetness. The neotrehalose can be used both orally and parenterally, and it is well metabolized by a recipient when used as an energy supplement without fear of toxicity or undesirable side effects. Crystalline neotrehalose readily dissolves in water but is substantially non-hygroscopic, so that it can be handled easily. Neotrehalose has a satisfactory chemical stability, and possess other desirable properties, including osmosis-regulating activity, is useful as a filler, imparts gloss, retains moisture, imparts viscosity, prevents crystallization of other saccharides, and is substantially not fermentable. These properties render neotrehalose useful in preparing a variety of compositions as a sweetener, taste-improving agent, quality-improving agent, and stabilizer.

Accordingly, the present method for preparing neotrehalose in industrially useful amounts has great significance in preparing food products, cosmetics and pharmaceuticals.

While there has been described what is at present considered to be the preferred embodiments of the invention, it will be understood that various modifications may be made therein, and it is intended to cover in the appended claims all such modifications as fall within the true spirit and scope of the invention.

We claim:

1. A process for preparing neotrehalose, consisting essentially of:

(a) hydrolyzing an amylaceous substance with a saccharogenic α-amylase to form a neotrehalose solution, wherein said α-amylase is obtained from *Bacillus subtilis* and has a higher saccharification power than dextrinogenic power, and wherein the amylaceous substance is crude starch or its partial hydrolysate having a dextrose equivalent of 70 or less; and (b) recovering neotrehalose from the neotrehalose solution.

2. The process of claim 1, wherein the concentration of said amylaceous substance is in the range of 1–80 w/w %, on a dry solid basis.

3. The process of claim 1, wherein the pH in step (a) is in the range of 3–9.

4. The process of claim 1, wherein the temperature in step (a) is in the range of 20°–80° C.

5. The process of claim 1, wherein the hydrolysis in step (a) takes 1–100 hours.

6. The process of claim 1, wherein the saccharogenic α-amylase is immobilized.

7. The process of claim 1, wherein the neotrehalose solution in step (a) contains about 5–15 w/w % neotrehalose on a dry solid basis.

8. A process for preparing crystallized neotrehalose consisting essentially of:

(a) hydrolyzing an amylaceous substance with a saccharogenic α-amylase to form a neotrehalose solution, wherein the α-amylase is obtained from *Bacillus subtilis* and has a higher saccharification power than dextrinogenic power, and wherein the amylaceous substance is crude starch or its partial hydrolysate having a dextrose equivalent of 70 or less;

(b) purifying and separating neotrehalose from the neotrehalose solution to obtain a neotrehalose-rich solution;

(c) recovering the neotrehalose-rich solution;

(d) concentrating the neotrehalose-rich solution to form a concentrate;

(e) crystallizing neotrehalose in the concentrate; and (f) recovering the crystallized crystallized neotrehalose.

9. The process of claim 8, wherein said purification consists essentially of at least one technique selected from the group consisting of fermentation using yeasts, membrane filtration, separatory sedimentation, crystallization, and column chromatography wherein a strongly-acidic action exchange resin is used.

10. A process for preparing a neotrehalose-containing composition consisting essentially of:

(a) hydrolyzing an amylaceous substance with a saccharogenic α-amylase to form a neotrehalose solution, wherein the α-amylase is obtained from *Bacillus subtilis* and has a higher saccharification power than dextrinogenic power, and wherein the amylaceous substance is crude starch or its partial hydrolysate having a dextrose equivalent of 70 or less;

(b) recovering neotrehalose from the neotrehalose solution; and (c) incorporating the neotrehalose into a carrier selected from the group consisting of edible carriers, cosmetically acceptable carriers, and pharmaceutically acceptable carriers.

11. The process of claim 10, wherein the composition contains neotrehalose in an amount of at least 5 w/w % and less than 100 w/w %, on a dry solid basis.

12. The process according to claim 10 wherein the neotrehalose is incorporated into the carrier by at least one technique selected from the group consisting of mixing, kneading, dissolving, melting, soaking, coating, injecting, crystallizing, and solidifying.

* * * * *